United States Patent [19]

Phillips et al.

[11] Patent Number: 4,701,464

[45] Date of Patent: Oct. 20, 1987

[54] FLUOROPYRIDINYLMETHYL CYCLOPROPANECARBOXYLATE INSECTICIDES

[75] Inventors: Richard B. Phillips, Cranbury, N.J.; Ernest L. Plummer, Yardley; John F. Engel, both of Washington Crossing, both of Pa.

[73] Assignee: FMC Corporation, Philadelphia, Pa.

[21] Appl. No.: 740,606

[22] PCT Filed: Apr. 10, 1985

[86] PCT No.: PCT/US85/00641

§ 371 Date: Jun. 3, 1985

§ 102(e) Date: Jun. 3, 1985

[87] PCT Pub. No.: WO85/04553

PCT Pub. Date: Oct. 24, 1985

Related U.S. Application Data

[63] Continuation-in-part of Ser. No. 599,852, Apr. 13, 1984, abandoned.

[51] Int. Cl.$^4$ .................. C07D 213/55; A01N 43/40
[52] U.S. Cl. .................................. 514/345; 514/277; 514/352; 546/300; 546/302; 546/312; 546/342
[58] Field of Search ............... 546/302, 312, 342, 300; 514/277, 352, 345

[56] References Cited

U.S. PATENT DOCUMENTS

| | | | |
|---|---|---|---|
| 4,163,787 | 8/1979 | Malhotra et al. | 514/345 |
| 4,221,799 | 9/1980 | Van Heertum et al. | 514/345 |
| 4,338,326 | 7/1982 | Cain et al. | 514/351 |
| 4,357,335 | 11/1982 | Martel et al. | 514/345 |
| 4,357,336 | 11/1982 | Wong | 514/345 |
| 4,390,543 | 6/1983 | Malhotra et al. | 514/345 |
| 4,423,222 | 12/1983 | Ash et al. | 546/337 |
| 4,426,524 | 1/1984 | Plummer | 544/336 |
| 4,587,255 | 5/1986 | Ackermann et al. | 514/345 |

OTHER PUBLICATIONS

Roberts et al., Basic Principles of Organic Chemistry, pp. 560–561, Benjamin pub. (1965).
Sket, et al., J. Heterocyclic Chem., 15, 527 (1978).

Primary Examiner—Alan L. Rotman
Attorney, Agent, or Firm—R. L. Andersen; H. R. Ertelt; W. Schmonsees

[57] ABSTRACT

Insecticidal compounds of the formula

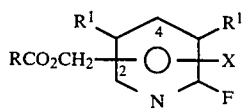

formulations thereof, their use for control of foliar or soil-borne insects, their method of preparation and certain novel intermediates for their preparation are disclosed and exemplified.

24 Claims, No Drawings

FLUOROPYRIDINYLMETHYL CYCLOPROPANECARBOXYLATE INSECTICIDES

This application is a continuation-in-part of application Ser. No. 599,852, filed Apr. 13, 1984, now abandoned.

The present invention relates to cyclopropanecarboxylate insecticides. More particularly it relates to cyclopropanecarboxylate insecticides in which the alcohol component is a substituted fluoropyridinylmethyl group, to a process for making them, to insecticidal compositions thereof, and to novel intermediates useful in the preparation of such insecticidal compounds.

In accordance with the present invention the insecticidal compounds of this invention are compounds of formula I:

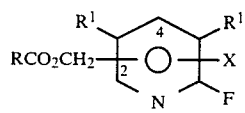

in which
X is hydrogen, halogen, particularly chlorine or fluorine, $C_{1-2}$alkoxy, phenoxy, or di($C_{1-2}$alkyl)amino;
R is 3-(2-chloro-3,3,3-trifluoropropenyl)-2,2-dimethylcyclopropyl;
3-(2,2-dihaloethenyl)-2,2-dimethylcyclopropyl;
3-(1,2-dibromo-2,2-dichloroethyl)-2,2-dimethylcyclopropyl;
2,2,3,3-tetramethylcyclopropyl; or 1-(4-chlorophenyl)-2-methylpropyl; and
$R^1$ is hydrogen or a halogen, particularly chlorine or fluorine.

These compounds have been found to be highly active for foliar or soil application for control of foliar insects or soil borne insects. Certain of the compounds of the invention are also highly active in controlling acarids. The wide versatility in uses for these compounds is highly unexpected and unusual for pyrethroid type compounds.

The invention includes compounds in which the carboxylate group is attached at position 2 or 4 of the pyridine ring, preferably position 4, or a mixture of compounds in which the carboxylate group is attached at positions 2 and 4.

It will be apparent to one skilled in the cyclopropanecarboxylate insecticide art that the insecticidal compounds have two asymmetric centers on the cyclopropane ring, thus providing the possibility for four isomers, two cis isomers and two trans isomers, and that various mixtures of these isomers, designated cis,trans also exist. It will also be apparent that some of the compounds also exist in the E and Z forms depending on the configuration about the vinyl group at the 3-position of the cyclopropane ring. Each of these isomers and configurations and all combinations of them are included in and form a part of the present invention.

Among the starting materials for preparation of the insecticides of this invention are tetrafluoropyridinylmethanols which may be made by the method of Sket and Zupan, *J. Heterocycl. Chem.*, 15, 527 (1978). This method produces a mixture of 2-hydroxymethyl and 4-hydroxymethyl isomers of tetrafluoropyridine. The mixture can be esterified without separation of isomers to produce the insecticidal compound of the invention having a corresponding mixture of isomers.

The 4-hydroxymethyl tetrafluoropyridine may also be separated from the mixture of isomers and used as the starting material for preparation of the 4-pyridinylmethyl esters of the invention.

This invention provides several novel intermediates which may be represented by formula II:

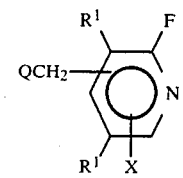

in which X is hydrogen, halogen, $C_{1-2}$-alkoxy, phenoxy, or di($C_{1-2}$-alkyl)amino or hydrazino; $R^1$ is hydrogen or a halogen; and Q is a leaving group. Suitable leaving groups, Q, in the aforesaid structural formula are known in the art today and include bromo, chloro, methylsulfonyl, and hydroxy. It is recognized that any leaving groups readily displaced by carboxylate anions are and will be functional equivalents for Q in the aforesaid formula. The insecticidal compounds of the invention may be prepared from these novel intermediates by esterification techniques, for example by reacting an acid chloride of the formula RCOCl or a carboxylic acid or salt of the formula RCOOM, in which R is as defined above and M is hydrogen or a cation, with an appropriately substituted fluoropyridinyl intermediate.

The following examples illustrate the foregoing methods of preparation.

EXAMPLE 1

SYNTHESIS OF A MIXTURE OF 2-HYDROXYMETHYL-3,4,5,6-TETRAFLUOROPYRIDINE AND 4-HYDROXYMETHYL-2,3,5,6-TETRAFLUOROPYRIDINE AS AN INTERMEDIATE

A mixture of 4.0 g (0.023 mole) of pentafluoropyridine and 8.8 g (0.048 mole) of benzophenone in 350 ml of nitrogen-degassed methanol was irradiated at room temperature in a Pyrex vessel for 48 hours using light between 300 nm and 350 nm in wavelength. The solution was concentrated under reduced pressure. The residue was dissolved in diethyl ether. This solution was successively washed twice with 50 ml of 5% aqueous sodium bicarbonate and once with 50 ml of water. After being dried over anhydrous sodium sulfate the solution was filtered and evaporated under reduced pressure, leaving a yellow oil as residue. This yellow oil was distilled to give 2.2 g of colorless oil, b.p. 56°-60° C./9 mm of Hg. Gas chromatographic analysis revealed that this oil consisted of 87% 4-hydroxymethyl-2,3,5,6-tetrafluoropyridine and 13% 2-hydroxymethyl-3,4,5,6-tetrafluoropyridine.

EXAMPLE 2

SYNTHESIS OF A MIXTURE OF (2,3,5,6-TETRAFLUOROPYRIDIN-4-YL)METHYL AND (3,4,5,6-TETRAFLUOROPYRIDIN-2-YL)METHYL CIS-3-(2-CHLORO-3,3,3-TRIFLUOROPROPENYL)-2,2-DIMETHYLCYCLOPROPANECARBOXYLATES

To a solution of 0.61 g (0.0025 mole) of cis-3-(2-chloro-3,3,3-trifluoropropenyl)-2,2-dimethylcyclopropanecarboxylic acid in 20 ml of dry diethyl ether containing one drop of dry dimethylformamide was added an ether solution of 0.55 g (0.0044 mole) of oxalyl chloride during a twenty minute period. The reaction mixture was stirred at room temperature for 0.5 hour. The solvent was evaporated under reduced pressure. Additional anhydrous diethyl ether (15 ml) was added to the residue, and this solvent was evaporated to remove excess oxalyl chloride. The crude product was dissolved in 20 ml of dry diethyl ether, and to this solution was added 0.5 g (0.003 mole) of the mixture of 4-hydroxymethyl-2,3,5,6-tetrafluoropyridine and 2-hydroxymethyl-3,4,5,6-tetrafluoropyridine (from Example 1) followed by the addition of 1 ml of anhydrous triethylamine. The reaction mixture was stirred at room temperature for twelve hours after which it was poured into 5% hydrochloric acid. This mixture was extracted three times with 35 ml of diethyl ether. The combined extracts were washed twice with 30 ml of water and once with 25 ml of a saturated aqueous sodium chloride solution. The extract was dried over anhydrous magnesium sulfate, filtered, and the solvent evaporated under reduced pressure, leaving an oil. This crude product was chromatographed on a Chromatotron (2 mm $SiO_2$ plate, 15% diethyl ether/hexane) and the higher $R_f$ material as illuminated by UV light was collected. The material collected was 90% (2,3,5,6-tetrafluoropyridin-4-yl)methyl cis-3-(2-chloro-3,3,3-trifluoropropenyl)-2,2-dimethyl-cyclopropanecarboxylate and 10% (3,4,5,6-tetrafluoropyridin-2-yl)methyl cis-3-(2-chloro-3,3,3-trifluoropenyl)-2,2-dimethylcyclopropanecarboxylate, Compound No. 1 of the tables below.

Analysis calc'd for $C_{15}H_{11}ClF_7NO_2$: C 44.41; H 2.73; N 3.45; Found: C 44.32; H, 2.66; N 3.18.

EXAMPLE 3

SYNTHESIS OF A MIXTURE OF (2,3,5,6-TETRAFLUOROPYRIDIN-4-YL)METHYL AND (3,4,5,6-TETRAFLUOROPYRIDIN-2-YL)METHYL CIS-3-(2,2-DICHLOROETHENYL)-2,2-DIMETHYLCYCLOPROPANECARBOXYLATES

By the method of Example 2, 0.50 g (0.0024 mole) of cis-3-(2,2-dichloroethenyl)-2,2-dimethylcyclopropanecarboxylic acid was reacted with 0.55 g (0.0044 mole) of oxalyl chloride. The resulting cis-3-(2,2-dichloroethenyl)-2,2-dimethylcyclopropanecarbonyl chloride was reacted with 0.53 g (0.0029 mole) of a mixture of 4-hydroxymethyl-2,3,5,6-tetrafluoropyridine and 2-hydroxymethyl-3,4,5,6-tetrafluoropyridine. Chromatographic separation (Chromatotron) of the reaction residue, a yellow oil, yielded 0.56 g of a white solid, mp 69°–71° C. This white solid was a mixture composed of 90% (2,3,5,6-tetrafluoropyridin-4-yl)methyl cis-3-(2,2-dichloroethenyl)-2,2-dimethylcyclopropanecarboxylate and 10% (3,4,5,6-tetrafluoropyridin-2-yl)methyl cis-3-(2,2-dichloroethenyl)-2,2-dimethylcyclopropanecarboxylate, Compound No. 4 of the tables below.

Analysis calc'd for $C_{14}H_{11}Cl_2F_4NO_2$: C 45.19; H 2.98; N, 3.76 Found: C 45.42; H, 2.78; N, 3.65.

EXAMPLE 4A

SYNTHESIS OF A MIXTURE OF (2,3,5,6-TETRAFLUOROPYRIDIN-4-YL)METHYL AND (3,4,5,6-TETRAFLUOROPYRIDIN-2-YL)METHYL CIS-3-(2,2-DIFLUOROETHENYL)-2,2-DIMETHYLCYCLOPROPANECARBOXYLATES

By the method of Example 2, 1.0 g (0.005 mole) of cis,trans-3-(2,2-difluoroethenyl)-2,2-dimethylcyclopropanecarbonyl chloride was reacted with 0.91 g (0.005 mole) of a mixture of 4-hydroxymethyl-2,3,5,6-tetrafluoropyridine and 2-hydroxymethyl-3,4,5,6-tetrafluoropyridine. The crude residue recovered from the reaction, weighing 1.6 g, was passed through a silica column using ether:hexane (1:49) to elute the fractions. The residue remaining after evaporation of solvent from the first fraction weighed 0.5 g and was shown by gas chromatography to contain 84% (2,3,5,6-tetrafluoropyridin-4-yl)methyl cis-3-(2,2-difluoroethenyl)-2,2-dimethylcyclopropanecarboxylate and 16% (3,4,5,6-tetrafluoropyridin-2-yl)methyl cis-3-(2,2-difluoroethenyl)-2,2-dimethylcyclopropanecarboxylate, Compound No. 7 of the tables below.

Analysis calc'd for $C_{14}H_{11}F_6NO_2$: C 49.56; H 3.24; N, 4.13. Found: C 50.46; H 3.32; N 4.45.

EXAMPLE 4B

SYNTHESIS OF A MIXTURE OF (2,3,5,6-TETRAFLUOROPYRIDIN-4-YL)METHYL AND (3,4,5,6-TETRAFLUOROPYRIDIN-2-YL)METHYL TRANS-3-(2,2-DIFLUOROETHENYL)-2,2-DIMETHYLCYCLOPROPANECARBOXYLATES

The residue from the second fraction (of Example 4A) weighed 0.4 g and was shown by gas chromatography to contain 50% (2,3,5,6-tetrafluoropyridin-4-yl)methyl trans-3-(2,2-difluoroethenyl)-2,2-dimethylcyclopropanecarboxylate and 50% (3,4,5,6-tetrafluoropyridin-2-yl)methyl trans-3-(2,2-difluoroethenyl)-2,2-dimethylcyclopropanecarboxylate, Compound 9 of the tables below.

Analysis calc'd for $C_{14}H_{11}F_6NO_2$: C 49.56; H 3.24; N 4.13; Found: C 50.36; H 3.29; N 4.50.

EXAMPLE 5

SYNTHESIS AND ISOLATION OF 4-HYDROXYMETHYL-2,3,5,6-TETRAFLUOROPYRIDINE

By the method of Example 1, 20.0 g (0.12 mole) of pentafluoropyridine and 33 g (0.18 mole) of benzophenone were irradiated in 1700 ml of methanol for approximately ninety hours. A brown oil weighing 26 g was recovered from the reaction mixture. Flash distillation of the brown oil produced 20 g of yellow oil which was redistilled under vacuum, yielding the following fractions:

| Fraction | Head Temperature (°C.) | Pressure (mm of Hg) |
| --- | --- | --- |
| 1 | 50–54 | 1.2 |
| 2 | 55–57 | 1.3 |
| 3 | 57–58 | 1.3 |
| 4 | 58 | 1.3 |

Fraction 4 was found to contain essentially pure 4-hydroxymethyl-2,3,5,6-tetrafluoropyridine.

EXAMPLE 6

SYNTHESIS OF (4-HYDROXYMETHYL-2,3,5-TRIFLUOROPYRIDIN-6-YL)HYDRAZINE AS AN INTERMEDIATE

To a solution of 1.0 g (0.0055 mole) of 4-hydroxymethyl-2,3,5,6-tetrafluoropyridine (from Example 5) in 50 ml of ethanol was added 0.2 g (0.004 mole) of hydrazine hydrate. This mixture was stirred for approximately twenty-four hours during which a white precipitate formed. The reaction mixture was filtered, and the filtrate was concentrated by evaporating the solvent under reduced pressure. Water and ether were added to this residue. The ether layer was separated, dried, and the solvent evaporated, leaving a yellow solid, (4-hydroxymethyl-2,3,5-trifluoropyridin-6-yl)hydrazine. The structure and nmr data are set forth in Table 1C.

EXAMPLE 7

SYNTHESIS OF 2-CHLORO-4-HYDROXYMETHYL-3,5,6-TRIFLUOROPYRIDINE AS AN INTERMEDIATE

To a solution of 0.35 g (0.0026 mole) of copper (II) chloride in 25 ml of concentrated hydrochloric acid was added slowly at room temperature 0.5 g (0.0026 mole) of (4-hydroxymethyl-2,3,5-trifluoropyridin-6-yl)hydrazine (from Example 6). This mixture was stirred at ambient temperature for two hours and was then refluxed for one hour. After being cooled, the reaction mixture was poured into water and was extracted with diethyl ether. The extract was dried over anhydrous magnesium sulfate, filtered, and the solvent evaporated under reduced pressure, leaving a brown, oily residue. This residue was passed through a short column of silica gel using a hexane/diethyl ether (50/50) mixture as eluant. The appropriate fractions were combined, and the solvent evaporated under reduced pressure, yielding 0.31 g of 2-chloro-4-hydroxymethyl-3,5,6-trifluoropyridine as a yellowish-brown liquid.

The structure and nmr spectra are set forth in Table 1C.

Analysis calc'd for $C_6H_3ClF_3NO$: C 36.46; H 1.52; N 7.09; Found: C 36.18; H 1.88; N 7.87.

EXAMPLE 8

SYNTHESIS OF (2-CHLORO-3,5,6-TRIFLUOROPYRIDIN-4-YL)METHYL CIS-3-(2-CHLORO-3,3,3-TRIFLUOROPROPENYL)-2,2-DIMETHYLCYCLOPROPANECARBOXYLATE

By the method of Example 2, 0.4 g (0.002 mole) of 2-chloro-4-hydroxymethyl-3,5,6-trifluoropyridine (from Example 7) was reacted with 0.54 g (0.002 mole) of cis-3-(2-chloro-3,3,3-trifluoropropenyl)-2,2-dimethylcyclopropanecarbonyl chloride to produce 0.35 g of (2-chloro-3,5,6-trifluoropyridin-4-yl)methyl cis-3-(2-chloro-3,3,3-trifluoropropenyl)-2,2-dimethylcyclopropanecarboxylate as a light yellow oil, Compound 14 in the Tables below.

Analysis calc'd for $C_{15}H_{11}Cl_2F_6NO_2$: C 42.65; H 2.61; N 3.32; Found: C 42.67; H 3.22; N 2.60.

EXAMPLE 9

SYNTHESIS OF 4-HYDROXYMETHYL-2,3,5-TRIFLUOROPYRIDINE

To a suspension of 0.7 g (0.0036 mole) of (4-hydroxymethyl-2,3,5-trifluoropyridin-6-yl)hydrazine (from Example 6) in 25 ml of distilled water was added a solution of 2.5 g (0.016 mole) of copper (II) sulfate during a 1.5 hour period. Nitrogen evolution continued while the reaction mixture was stirred at ambient temperature for two hours and while it refluxed for an additional two hours. After being cooled, the reaction mixture was extracted with diethyl ether. This extract was dried over anhydrous magnesium sulfate, filtered, and the solvent was evaporated under reduced pressure, leaving a brown oil. This oil was passed through a short column of silica gel using a mixture of diethyl ether and hexane (50/50) as eluant. The appropriate fractions were combined and the solvent evaporated under reduced pressure, yielding 0.3 g of 4-hydroxymethyl-2,3,5-trifluoropyridine as a yellow oil. The structure and nmr spectra for this compound are set forth in Table 1C.

Analysis calc'd for $C_6H_4F_3NO$: C 44.17; H 2.45; N 8.59; Found: C 44.70; H 2.99; N 8.55.

EXAMPLE 10

SYNTHESIS OF (2,3,5-TRIFLUOROPYRIDIN-4-YL)METHYL CIS-3-(2-CHLORO-3,3,3-TRIFLUOROPROPENYL)-2,2-DIMETHYLCYCLOPROPANECARBOXYLATE

By the method of Example 2, 0.3 g (0.002 mole) of 4-hydroxymethyl-2,3,5-trifluoropyridine (from Example 9) was reacted with 0.5 g (0.002 mole) of cis-3-(2-chloro-3,3,3-trifluoropropenyl)-2,2-dimethylcyclopropanecarbonyl chloride to produce 0.35 g of (2,3,5-trifluoropyridin-4-yl)methyl cis-3-(2-chloro-3,3,3-trifluoropropenyl)-2,2-dimethylcyclopropanecarboxylate as a clear, yellow oil, Compound 15 of the tables below.

Analysis calc'd for $C_{15}H_{12}ClF_6NO_2$: C 46.45; H 3.10; N 3.6; Found: C 46.37; H 3.22; N 3.0.

EXAMPLE 11

SYNTHESIS OF 4-HYDROXYMETHYL-2-METHOXY-3,5,6-TRIFLUOROPYRIDINE AS AN INTERMEDIATE

A mixture of 1.0 g (0.0055 mole) of 4-hydroxymethyl-2,3,5,6-tetrafluoropyridine (from Example 5) and 0.30 g (0.0055 mole) of sodium methoxide in 25 ml of methanol was refluxed for approximately twenty hours. After being cooled, the reaction mixture was poured into water. The aqueous solution was extracted with diethyl ether. The diethyl ether extract was dried over anhydrous magnesium sulfate, filtered, and the solvent evaporated under reduced pressure, yielding 0.85 g of 4-hydroxymethyl-2-methoxy-3,5,6-trifluoropyridine as a yellow oil. The structure and nmr spectra are set forth in Table 1C below.

Analysis calc'd for $C_7H_6F_3NO_2$: C 43.52; H 3.11; N 7.25; Found: C 43.10; H 3.11; N 7.12.

EXAMPLE 12

SYNTHESIS OF (2-METHOXY-3,5,6-TRIFLUOROPYRIDIN-4-YL)METHYL CIS-3-(2-CHLORO-3,3,3-TRIFLUOROPROPENYL)-2,2-DIMETHYLCYCLOPROPANECARBOXYLATE

By the method of Example 2, 0.5 g (0.003 mole) of 4-hydroxymethyl-2-methoxy-3,5,6-trifluoropyridine (from Example 11) was reacted with 0.7 g (0.003 mole) of cis-3-(2-chloro-3,3,3-trifluoropropenyl)-2,2-dimethylcyclopropanecarbonyl chloride to produce a clear oil, Compound 16 of tables below.

Analysis calc'd for $C_{16}H_{14}ClF_6NO_3$: C 45.98; H 3.35; N 3.35; Found: C 45.89; H 3.51; N 3.00.

EXAMPLE 13

SYNTHESIS OF 2-DIMETHYLAMINO-4-HYDROXYMETHYL-3,5,6-TRIFLUOROPYRIDINE AS AN INTERMEDIATE

A mixture of 1.0 g (0.0055 mole) of 4-hydroxymethyl-2,3,5,6-tetrafluoropyridine (from Example 5) and 0.23 g (0.0050 mole) of dimethylamine in 25 ml of ethanol was refluxed for approximately twenty hours. The reaction mixture was cooled and was poured into water. This mixture was extracted with diethyl ether. The extract was dried over anhydrous magnesium sulfate, filtered, and the solvent evaporated under reduced pressure, yielding 0.9 g of 2-dimethylamino-4-hydroxymethyl-3,5,6-trifluoropyridine as a yellow oil. The structure and nmr spectra are set forth in Table 1C below.

Analysis calc'd for $C_8H_9F_3N_2O$: C 46.60; H 4.37; N 13.59; Found: C 47.18; H 4.42; N 14.51.

EXAMPLE 14

SYNTHESIS OF (2-DIMETHYLAMINO-3,5,6-TRIFLUOROPYRIDIN-4-YL)METHYL CIS-3-(2-CHLORO-3,3,3-TRIFLUOROPROPENYL)-2,2-DIMETHYLCYCLOPROPANECARBOXYLATE

By the method of Example 2, 0.5 g (0.002 mole) of 2-dimethylamino-4-hydroxymethyl-3,5,6-trifluoropyridine (from Example 13) was reacted with 0.6 g (0.002 mole) of cis-3-(2-chloro-3,3,3-trifluoropropenyl)-2,2-dimethylcyclopropanecarbonyl chloride to produce, after purification through a short silica gel column and the Chromatotron, 0.45 g of (2-methoxy-3,5,6-trifluoropyridin-4-yl)methyl cis-3-(2-chloro-3,3,3-trifluoropropenyl)-2,2-dimethylcyclopropanecarboxylate as an oil, Compound No. 20 of the tables below.

Analysis calc'd for $C_{17}H_{17}ClF_6N_2O_2$: C 47.38; H 3.95; N 6.50; Found: C 47.69; H 4.09; N. 6.55.

EXAMPLE 15

SYNTHESIS OF 3,5-DICHLORO-2,6-DIFLUORO-4-HYDROXYMETHYLPYRIDINE AS AN INTERMEDIATE

Step A: Synthesis of 4-cyano-3,5-dichloro-2,6-difluoropyridine

To a mixture of 40.4 g (0.200 mole) of 3,5-dichloro-2,4,6-trifluoropyridine in 50 ml of dimethylformamide that had been cooled to 0° C. was added slowly 10 g (0.20 mole) of sodium cyanide. After addition was complete the reaction was stirred at 0° C. for two hours and at room temperature of two hours. The dimethylformamide was distilled from the reaction mixture under reduced pressure, and the black residue was mixed with 200 ml of water. This mixture was extracted with ethyl acetate. The extracts were combined, and the ethyl acetate was evaporated, leaving a black residue weighing approximately 15 g. This residue was distilled, yielding approximately 10 g of 4-cyano-3,5-dichloro-2,6-difluoropyridine as a white solid.

The ir and nmr spectra were consistent with the proposed structure.

Step B: Synthesis of 3,5-dichloro-2,6-difluoropyridine-4-carboxaldehyde

To a mixture, of 10.1 g (0.048 mole) of 4-cyano-3,5-dichloro-2,6-difluoropyridine (from Step A) in 50 ml of toluene that had been cooled to 0° C. was added 6.9 g (0.049 mole) of diisobutylaluminum hydride. After complete addition the reaction mixture was allowed to warm to room temperature and was stirred for approximately seventeen hours. A mixture of methanol and petroleum ether (2:1) was added to the reaction mixture which was then acidified with dilute sulfuric acid. The organic layer was separated from the aqueous layer and was dried over anhydrous sodium sulfate. After being filtered, the solvent was evaporated under reduced pressure, leaving 6.0 g of 3,5-dichloro-2,6-difluoropyridine-4-carboxaldehyde as a residue.

The ir and nmr spectra were consistent with the proposed structure.

Step C: Synthesis of 3,5-dichloro-2,6-difluoro-4-hydroxymethylpyridine

To a mixture of 5.0 g (0.024 mole) of 3,5-dichloro-2,6-difluoropyridine-4-carboxaldehyde (from Step B) in 100 ml of ethanol that had been cooled to 0° C. was added slowly 1.4 g (0.037 mole) of sodium borohydride. After complete addition the reaction mixture was allowed to warm to room temperature and was stirred for approximately seventeen hours. The reaction mixture was quenched with a stoichiometric amount of glacial acetic acid, and the ethanol was evaporated under reduced pressure, leaving a residue. This residue was mixed with dilute hydrochloric acid, and this mixture was extracted with diethyl ether. The combined extracts were washed repeatedly with a 5% aqueous solution of sodium bicarbonate. The extract was dried over anhydrous sodium sulfate and filtered. The solvent was evaporated under reduced pressure, leaving 3.0 g of 3,5-dichloro-2,6-difluoro4-hydroxymethylpyridine as a residue.

The ir and nmr spectra were consistent with the proposed structure.

EXAMPLE 16

SYNTHESIS OF (3,5-DICHLORO-2,6-DIFLUOROPYRIDIN-4-YL)METHYL CIS-3-(2-CHLORO-3,3,3-TRIFLUOROPROPENYL)-2,2-DIMETHYLCYCLOPROPANECARBOXYLATE

By The method of Example 2, 0.6 (0.002 mole) of 3,5-dichloro2,6-difluoro-4-hydroxymethylpyridine (Example 15) was reacted with 0.61 g (0.002 mole) of cis-3-(2-chloro-3,3,3-trifluoropropenyl)-2,2-dimethylcyclopropanecarbonyl chloride to produce, after purification using the Chromatotron, 0.5 g of (3,5-dichloro-2,6-difluoropyridin-4-yl)methyl cis-3-(2-chloro-3,3,3-trifluoropropenyl)-2,2-dimethylcyclopropanecarboxylate as a clear, white liquid, compound 21 in the Tables below.

The ir and nmr spectra were consistent with the proposed structure.

Analysis calc'd for $C_{14}H_{11}Cl_3F_5NO_2$: C 41.05; H 2.51; N 3.19 Found: C 41.54: H 2.32; N 2.89.

EXAMPLE 17

SYNTHESIS OF (3,5-DICHLORO-2,6-DIFLUOROPYRIDIN-4-YL)METHYL CIS-3-(2,2-DICHLOROETHENYL)-2,2-DIMETHYLCYCLOPROPANECARBOXYLATE

By the method of Example 2, 0.5 g (0.002 mole) of 3,5-dichloro-2,6-difluoro-4-hydroxymethylpyridine (Example 15) was reacted with 0.5 g (0.002 mole) of cis-3-(2,2-dichloroethenyl)-2,2-dimethylcyclopropanecarbonyl chloride to produce, after purification using the Chromatotron, 0.3 g of (3,5-dichloro-2,6-difluoropyridin-4-yl)methyl cis-3-(2,2-di-chloroethenyl)-2,2-dimethylcyclopropanecarboxylate, compound 22 in the Tables below.

The ir and nmr spectra were consistent with the proposed structure.

EXAMPLE 18

SYNTHESIS OF 4-HYDROXYMETHYL-2-PHENOXY-3,5,6-TRIFLUOROPYRIDINE AS AN INTERMEDIATE

To a solution of 5.0 g (0.028 mole) of 4-hydroxymethyl-2,3,5,6-tetrafluoropyridine in 50 ml of tetrahydrofuran was added 0.64 g (0.028 mole) of sodium metal. The reaction mixture was stirred at room temperature for three hours after which 2.6 g (0.028 mole) of phenol was added, and the mixture refluxed for twenty-one hours. The reaction was cooled to room temperature and then acidified with 10% hydrochloric acid. The resulting solution was extracted with diethyl ether. The combined extracts were dried over anhydrous sodium sulfate, filtered, and the solvent was evaporated under reduced pressure, leaving a yellow oil. This yellow oil was chromatographed through silica gel, yielding 4-hydroxymethyl-2-phenoxy-3,5,6-trifluoropyridine as a clear, yellow liquid. The proton nmr and ir spectra were consistent with the proposed structure.

EXAMPLE 19

SYNTHESIS OF (2-PHENOXY-3,5,6-TRIFLUOROPYRIDIN-4-YL)METHYL CIS-3-(2-CHLORO-3,3,3-TRIFLUOROPROPENYL)-2,2-DIMETHYLCYCLOPROPANECARBOXYLATE

By the method of Example 2,0.5 g (0.0019 mole) of cis-3-(2-chloro-3,3,3-trifluoropropenyl)-2,2-dimethylcyclopropanecarbonyl chloride was reacted with 0.5 g (0.0020 mole) of 4-hydroxymethyl-1-phenoxy-3,5,6-trifluoropyridine to produce 0.6 g of (2-phenoxy-3,5,6-trifluoropyridin-4-yl)methyl cis-3-(2-chloro-3,3,3-trifluoropropenyl)-2,2-dimethylcyclopropanecarboxylate as a colorless oil compound 23 in the Tables below. The ir and nmr spectra were consistent with the proposed structure.

EXAMPLE 20

SYNTHESIS OF 2-BROMOETHYL-6-FLUOROPYRIDINE AS AN INTERMEDIATE

A mixture of 10 g (0.09 mole) of 2-fluoro-6-methylpyridine and 16 g (0.09 mole) of N-bromosuccinimide in 90 ml of carbon tetrachloride was refluxed for one hour using a sunlamp as heat and light source. The reaction mixture was cooled and filtered. The solvent was evaporated from the filtrate under reduced pressure, leaving 16 g of a brown liquid as residue. This brown liquid was distilled into the following fractions:

| Fraction | Head Temperature | Pressure |
|---|---|---|
| 1 | 25–35° C. | <1 mm |
| 2 | 80–82° C. | 0.9 mm |
| 3 | 83–91° C. | 0.9 mm |
| 4 | 91–92° C. | <1 mm |

Fractions 2 and 3 were >96% pure 2-bromomethyl-6-fluoropyridine and were therefore combined. Fraction 4 was composed of a 1:1 mixture of 2-bromomethyl-6-fluoropyridine and 2-dibromomethyl-6-fluoropyridine. The nmr spectra was consistent with the proposed structure for Fractions 2 and 3.

EXAMPLE 21

SYNTHESIS OF (6-FLUOROPYRIDIN-2-YL)METHYL CIS-3-(2-CHLORO-3,3,3-TRIFLUOROPROPENYL)-2,2-DIMETHYLCYCLOPROPANECARBOXYLATE

To a mixture 0.970 g (0.004 mole) of cis-3-(2-chloro-3,3,3-trifluoropropenyl)-2,2-dimethylcyclopropanecarboxylic, acid and 0.609 g (0.004 mole) of 1,8-diazabicyclo[5.4.0]undec-7-ene in 15 ml of acetonitrile was added under nitrogen 0.75 g (0.004 mole) of 2-bromomethyl-6-fluoropyridine (Example 20). The reaction mixture was stirred for approximately sixteen hours after which it was diluted with diethyl ether. This mixture was extracted twice with 150 ml of 1N hydrochloric acid and once with 150 ml of a saturated aqueous solution of sodium chloride. After drying the organic phase over anhydrous sodium sulfate, it was filtered, and the solvent was evaporated under reduced pressure, leaving an orange oil as residue. This oil was purified on a Chromatotron using methylene chloride/hexane (3/1) as eluant. The proper fractions were combined, and the solvent was evaporated, leaving 0.92 g of (6-fluoropyridin-2-yl)methyl cis-3-(2-chloro-3,3,3-trifluoropropenyl)-2,2-dimethylcyclopropanecarboxylate, compound 26 in the Tables below. The ir and nmr spectra were consistent with the proposed structure.

Analysis calc'd for $C_{15}H_{14}ClF_4O_2N$: C: 51.23; H: 4.01; Found: C: 48.04; H: 3.45.

EXAMPLE 22

SYNTHESIS OF 4-BROMOMETHYL-2-FLUOROPYRIDINE AS AN INTERMEDIATE

By the method of Example 20, 10 g (0.09 mole) of 2-fluoro-4-methylpyridine and 16 g (0.09 mole) of N-bromosuccinimide were reacted in 90 ml of carbon tetrachloride to produce 4.18 g 4-bromomethyl-2- fluoropyridine. The ir, proton nmr, and $^{19}F$ nmr spectra were all consistent with the proposed structure.

EXAMPLE 23

SYNTHESIS OF (2-FLUOROPYRIDIN-4-YL)METHYL CIS-3-(2-CHLORO-3,3,3-TRIFLUORO-PROPENYL)-2,2-DIMETHYLCYCLO-PROPANECARBOXYLATE

By the method of Example 21, 0.970 g (0.004 mole) of cis-3-(2-chloro-3,3,3-trifluoropropenyl)-2,2-dimethylcyclopropanecarboxylic acid and 0.75 g (0.004 mole) of 4-bromomethyl-2-fluoropyridine (Example 22) were reacted in the presence of 0.609 g (0.004 mole) of 1,8-diazabicyclo[5.4.0]undec-7-ene in 20 ml of acetonitrile to produce 1.09 g of (2-fluoropyridin-4-yl)methyl cis-3-(2-chloro-3,3,3-trifluoropropenyl)-2,2-dimethylcyclopropanecarboxylate, compound 28 in the Tables below. The ir, proton nmr, and 19c nmr spectra were all consistent with the proposed structure.

Analysis calc'd for $C_{15}H_{14}ClF_4O_2N$: C: 51.23; H: 4.01; Found: C: 50.47; H: 3.83.

The compounds of the invention were tested for biological activity as described below.

Initial Southern Corn Rootworm Activity

A stock solution of the test compound was prepared by dissolving 4.8 mg in 10 ml of acetone and diluting with 90 ml of acetone/water (1:9). The addition of 5 ml of this stock solution to 30 g of air-dried, clay loam soil in a 3 oz plastic cup provided a concentration of 8 ppm of the test compound in the soil. Serial dilution of the stock solution was used to provide concentrations of the test compound in soil of 4, 2, 1, 0.5, and 0.125 ppm. In all cases 5 ml of a solution having the required concentration was added to 30 g of soil. The treated soil was allowed to stand uncovered in a hood for 0.5 hour to evaporate the acetone. Before infesting the soil with southern corn rootworm larvae, the soil was mixed thoroughly and two three-day-old corn sprouts were placed in the cup. Ten early third-stage (9-10 days old) southern corn rootworm larvae (*Diabratica undecimpunctita howardi* Barber) were placed in the cup which was then covered with a plastic lid and placed in a closed plastic bag. After storage at 74°-78° F. for 48 hours, the mortality of the larvae was determined by removing the cup from the plastic bag, removing the cover, and placing the cup in a modified Berlese polyethylene funnel fitted with an 18-mesh screen. The funnels were placed over containers of an aqueous detergent solution. Incandescent lights (100 watts) were placed 36 cm above the soil samples. The heat from these lights slowly dried the soil causing larvae that had not been effected by the test compound to emerge from the soil and drop into the detergent solution. The percent mortality was determined in this manner for each concentration. Duplicate tests were run at each concentration. The results of these tests, shown in Table 2, demonstrate outstanding initial activity against southern corn rootworm.

Residual Southern Corn Rootworm Activity

The residual activity of the test compounds was determined in the same manner as the initial activity except that treated soil was not infested with larvae until 7, 14, 28, and 42 days after treatment, the usual concentration of test compound being 4 ppm. Whenever the mortality dropped below 20% at 7 or 14 days, the remainder of the test was not run. Many of the compounds had excellent residual activity as shown by the results in Table 3.

Foliar Insecticide Activity

Test compounds were dissolved in a mixture containing 10% acetone, 0.25% octylphenoxypolyethoxyethanol, and 89.75% water to give a solution containing 1000 ppm of the compound. This solution was sprayed on the upper and lower surfaces of the leaves of the green test plants to run-off. After spraying, the plants were allowed to dry. Two replicates of each compound were run for each species.

Insecticidal activity against the pea aphid (*Acyrthosiphon pisum*) was tested by placing a broad bean plant which had been sprayed and had dried into a 1400 cup. Each plant was infested with ten aphids, and the cups were then capped. Mortality was determined 48 hours after treatment.

Pinto bean plants were used for tests against the Mexican bean beetle (*Epilachna varivestis*) and the southern armyworm (*Spodoptera eridania*). For both species treated leaves were removed from the plants and placed in paper cups. Ten individuals of one species were placed in a cup and the cup was then capped. Mortality was recorded 48 hours after treatment.

The twospotted spider mite (*Tetranychus urticae*) was also tested on pinto beans. The plants were infested by placing a section of a leaf taken from an infested plant onto the test plant to be infested. Approximately 75 mites were used. The test plants were sprayed after infestation and were placed on a shelf at ambient conditions for 48 hours. Mortality was determined at the conclusion of this period.

The results shown in Table 4 show the compounds are highly active against each species against which they were tested.

In accordance with the composition aspect of the invention, the compounds are generally not applied full strength but are typically applied as formulations which may be applied as such or further diluted for application. Typical formulations include compositions of the active ingredients in combination with one or more agriculturally acceptable adjuvants, carriers or diluents, preferably with a surface active agent, and optionally with other active ingredients. Suitable formulations include solid compositions such as dusts, wettable powders, and granules or liquid compositions such as solutions, dispersions, suspensions, and emulsifiable concentrates, the choice varying with the type of pest and environmental factors present at the particular locus of infestation.

A typical formulation may vary widely in concentration of active ingredients and other ingredients depending upon the particular agent used, the additives and carriers used, other active ingredients, the desired mode of application, and numerous other factors well known to those skilled in formulating compositions for use in agriculture.

With due consideration to these factors, the active ingredient of a typical formulation may, for example, comprise 0.01 percent to 1 percent by weight up to about 95 percent by weight, preferably 1 percent up to 90 or 95 percent by weight, of the formulation. Agriculturally acceptable carriers, diluents, adjuvants, surface active agents, and optionally other suitable active ingredients comprise the balance of the formulation. Thus a typical formulation may contain from 0.01 to 95 (preferably 1 to 95) percent by weight active ingredient, from 0 to 30 percent by weight surface active agent, and from 5 to 99.99 (preferably 5 to 99) percent by weight of an inert agriculturally acceptable carrier or diluent.

Provided below is a general description of exemplary types of formulations which may be employed for application of the compounds of the present invention.

SOLIDS OR DRY FORMULATIONS

Dry formulations are mixtures of a liquid or solid active ingredient with a solid carrier to form a particulate product comprising discrete solid particles of various sizes. Solid or dry compositions may take the form of dusts, wettable powders and granules having average particle sizes varying from about 5 microns to about 5000 microns. These compositions employ solid or dry carriers and/or diluents which may be selected from one or more of the following:

1. Attapulgite Clay: Characterized as hydrated aluminum-magnesium silicate, with or without free water, and possessing sorptive capacity of at least 35% w/w.
2. Kaolin or Kaolinite Clay: Characterized as hydrated aluminum silicate, and including the species dickite, nakrite, and halloysite, and further characterized by having low values for cation exchange capacity.
3. Montmorillonite: Characterized as hydrous aluminum silicate derived by natural modification of mica and pyrophyllite, and further sub-divided into swelling (sodium form) and non-swelling (calcium form).
4. Pyrophyllite (Talc): Characterized as hydrous magnesium or aluminum silicate and having neutral to basic pH, and further characterized by low to moderate sorptive capacity.
5. Diatomite: Class of opaline silica skeletal remains of aquatic species which includes diatomaceous earth, tripolite, kieselguhr, and fossil flour, characterized by high (85-93%) silica content, and having high absorptive and low adsorptive capacity.
6. Silica: Diverse origin materials characterized by very high (98-100%) silica content and high (75-100%) sorptive capacity (synthetic), or low sorptive capacity, such as sand.
7. Botanicals: Any material of plant origin capable of being processed into particles of the desired size, including nut shell flours, wood and cellulose flours, corncobs, and the like.
8. Calcium Carbonate Dust formulations are finely divided solid compositions of active ingredient in admixture with a solid carrier. In most cases dust formulations have an average particle size of less than about 50 microns, typically 5 to 40 microns, an active ingredient content of 1 to 30 percent by weight, and from 70 to 99 percent by weight of one or more of the solid diluents or carriers described above. Since dust formulations are generally applied as such or mixed with other solids for application, they generally do not require a surface active agent or other adjuvants. The following exemplify typical dust formulations:

| | % W/W |
|---|---|
| 1% Dust | |
| Active Ingredient | 1.0 |
| Finely Divided Silica | 99.0 |
| | 100.0 |
| 10% Dust | |

| | % W/W |
|---|---|
| Active Ingredient | 10.0 |
| Kaolin | 90.0 |
| | 100.0 |
| 30% Dust | |
| Active Ingredient | 30.0 |
| Montmorillonite | 30.0 |
| Talc | 40.0 |
| | 100.0 |

Wettable powders are finely divided solid compositions which disperse readily in water or other liquid vehicles. The wettable powder may be applied as a dry dust or as a dispersion in water or other liquid. Thus, wettable powders are essentially a dust or powder formulation containing a surface active agent in addition to the active ingredient and solid carrier normally employed in dusts.

A wettable powder may thus typically contain from 1 to 95 percent by weight active ingredient, from 1 to 15 percent surface active agent, and from 4 to 98 percent by weight of one or more of the inert solid or dry carriers or diluents described above.

Suitable surface active agents may be selected from the following:

1. Salts or esters of sulfated or sulfonated fatty acids.
2. Salts or esters of ethylene oxide condensates of sulfated or sulfonated fatty acids.
3. Salts of amine derivatives of various resin and fatty acids including, but not restricted to, palmitic and myristic acids, tall oils, and taurine.
4. Salts of alkylarylsulfonates including alkylnaphthalenesulfonates and dialkylnaphthalenesulfonates.
5. Ethylene oxide condensates of mixed fatty and resin acids.
6. Ethylene oxide condensates of linear or branched chain glycols, secondary alcohols, or alkylaryl alcohols.
7. Mixed ethylene oxide and propylene oxide condensates of linear and branched chain glycols.
8. Salts of sulfonated naphthalene-formaldehyde condensates.
9. Salts of carboxylated poly-electrolytes.
10. Salts of polymerized alkylnaphthalenesulfonic acids.
11. Salts of lignin sulfonates.
12. Fatty alcohol polyglycol ethers.
13. Materials of classes 1, 2, 5, 6, 7 above when sorbed onto a sorptive, water compatible carrier.
14. Inorganic salts such as tripolyphosphate and hexametaphosphate.
15. Salts and esters of orthophosphoric acid.
16. Fatty acid esters of sorbitan.
17. Ethylene oxide condensates with fatty acid esters of sorbitan.
18. Alkylated alkene mono- and polyhydric alcohols.
19. Sulfonated castor oil.
20. Ethylene oxide condensate with lanolin.
21. Coconut alkanolamides.
22. Sulfated sperm oil.
23. Salts of linear alkyl sulfonates
24. Tall oil ethoxylates.

The following are typical wettable powders:

| | % W/W |
|---|---|
| 1% Powder | |

| | % W/W |
|---|---|
| Active Ingredient | 1.0 |
| Sodium lignosulfonate | 7.5 |
| Sodium laurylsulfate | 1.5 |
| Talc | 96.0 |
| Total | 100.0 |
| 5% Powder | |
| Active Ingredient | 5.0 |
| Sodium lignosulfonate | 1.5 |
| Sodium alkylnaphthylene sulfonate | 1.5 |
| Attaclay | 92.0 |
| Total | 100.0 |
| 25% Powder | |
| Active Ingredient | 25.0 |
| Sodium lignosulfonate | 1.5 |
| Sodium laurylsulfate | 1.5 |
| Montmorillonite | 72.0 |
| Total | 100.0 |
| 90% Powder | |
| Active Ingredient | 90.0 |
| Sodium dibutylnaphthalene-sulfonate | 0.5 |
| Sodium lignosulfonate | 3.5 |
| Kaolin clay | 6.0 |
| Total | 100.0 |

Granules are solid or dry compositions of active ingredient deposited on or in a large particle. Granules usually have an average particle size in the range of 150 to 5000 microns, typically 425 to 850 microns. Granular formulations generally contain from 1 to 50 percent by weight of active ingredient, from 1 to 15 percent by weight of one or more of the surface active agents described above, and from 50 to 98 percent by weight of one or more of the inert solid or dry carriers or diluents described above.

Granular formulations may be of several types. Impregnated granules are those in which the active ingredient is applied, normally as a solution, to large particles of an absorbent diluent or carrier such as attapulgite or kaolin clay, corncobs or expanded mica. Surface coated granules are granules produced by adhering an active ingredient in finely divided form on the surface of a generally non-absorbent particle or by applying a solution of active ingredient to the surface of such a carrier. The carrier or core may be water soluble, such as prilled fertilizer or urea, or insoluble, such as sand, marble chips, corncobs, or coarse talc, as described above. Particularly useful are granules wherein a wettable powder is adhered as a surface coating to a sand or other insoluble particle, so that the wettable powder may be dispersed on contact of the granule with moisture. Granules may also be produced by agglomeration of dusts or powders, by compaction, by extrusion through a die, or by use of a granulation disk.

The following are typical granular formulations:

| | % W/W |
|---|---|
| 1% Granule | |
| Active Ingredient | 1.0 |
| Attapulgite | 99.0 |
| Total | 100.0 |
| 5% Granule | |
| Active Ingredient | 5.0 |
| Attapulgite | 95.0 |
| Total | 100.0 |

The granules above may be prepared by dissolving the active ingredient in a volatile solvent such as methylene chloride, coating large particles of attapulgite clay with the solution, then allowing the solvent to evaporate.

As indicated above, granules may also be adhered to a nonabsorbent core material. The following are typical formulations:

| | | % W/W |
|---|---|---|
| 5% Sand-Core Granule | | |
| 75% Powder Base | | 6.64 |
| Active compound | 75.0 | |
| Sodium alkylnaphthalene-sulfonate | 1.0 | |
| Sodium lignosulfonate | 4.0 | |
| Barden clay | 20.0 | |
| Dilute Polyvinylacetate | | 1.75 |
| Silica (425-850) | | 91.61 |
| Total | | 100.00 |
| 47.5% Sand-Core Granule | | |
| 95% Powder Base | | 50.0 |
| Active compound | 95.0 | |
| Sodium alkylnaphthalene-sulfonate | 1.0 | |
| Sodium lignosulfonate | 4.0 | |
| Dilute Polyvinylacetate adherent | | 2.0 |
| Silica (425-850) | | 48.00 |
| Total | | 100.00 |

The foregoing sand-core granules may be prepared by incorporating the active compound into the base, then adhering the base to sand, utilizing an adhesive such as polyvinylacetate to assure adhesion.

LIQUID AND SEMI-LIQUID FORMULATIONS

Liquid formulations are those which contain the active ingredients dissolved or dispersed in one or more inert liquid carriers or diluents, containing from 0.01 to about 95% active ingredients. Carriers suitable for use in liquid formulations may be selected from the following:
1. Water
2. Aliphatic petroleum solvents including kerosene, light refined mineral oils, and diesel oils.
3. Aromatic petroleum solvents including coal tar fractions yielding xylene, toluene, and benzene; light, medium, and heavy aromatic naphthas; and alkylated mixed naphthenics.
4. Alcohols such as ethanol and isopropyl alcohol.
5. Alkyl ethers of glycols.
6. Esters including dibutyl phthalate, di-2-ethylhexyl phthalate, and ethyl acetate.
7. Ketones including cyclohexanone, methyl isobutyl ketone, acetone, diacetone, and isophorone.
8. Chlorinated hydrocarbons including ethylene dichloride, methylene chloride, chlorobenzene, chlorinated toluene, and chlorinated xylene.
9. Vegetable oils including cottonseed, soybean, pine, sesame, and palm oils.
10. Aqueous solutions of natural origin such as liquors obtained in processing natural sugar products, and fermentation broths.

Solutions are liquid compositions containing from about 0.01 to 95 percent by weight active ingredient and from 1 to 99.99 percent by weight of one or more of the inert liquid diluents or carriers described above. These may be applied as such or further diluted for application.

Suspensions or dispersions (also sometimes called flowable formulations) are liquid formulations containing from 0.01 to 95 percent by weight active ingredient and from 1 to 99.99 percent by weight of an inert liquid diluent or carrier, in which the active ingredient is wholly or partially insoluble in the diluent or carrier at the concentration level employed. Suspension or dispersion is frequently facilitated by incorporating from 1 to 30 percent by weight of one or more surface active agents described above, alone or together with a thickner or suspending agent. Like solutions, dispersions may be used as such or further diluted with a liquid carrier for application.

The following illustrate suspensions suitable for use in the present invention:

|  | % W/W |
|---|---|
| 25% Oil Suspension: | |
| Active ingredient | 25.0 |
| polyoxyethylene sorbitol hexaoleate | 5.0 |
| aliphatic hydrocarbon oil | 70.0 |
| Total | 100.0 |
| 1% Aqueous Suspension: | |
| Active ingredient | 1.0 |
| Polyacrylic acid thickener | 0.3 |
| Sodium alkylnapthalenesulfonate | 1.0 |
| Sodium lignosulfonate | 4.0 |
| Polyvinyl alcohol suspending agent | 1.0 |
| Water | 92.7 |
| Total | 100.0 |
| 20% Aqueous Suspension: | |
| Active ingredient | 20.0 |
| Polyacrylic acid thickener | 0.3 |
| Sodium alkylnapthalenesulfonate | 1.0 |
| Sodium lignosulfonate | 4.0 |
| Polyvinyl alcohol suspending agent | 1.0 |
| Water | 73.7 |
| Total | 100.0 |
| 40% Aqueous Suspension: | |
| Active ingredient | 40.0 |
| Polyacrylic acid thickener | 0.3 |
| Dodecylphenol polyethylene glycol ether | 0.5 |
| Disodium phosphate | 1.0 |
| Monosodium phosphate | 0.5 |
| Polyvinyl alcohol | 1.0 |
| Water | 56.7 |
| Total | 100.0 |

Emulsifiable concentrates (EC's) are homogeneous liquid compositions, containing the active ingredient dissolved in a liquid carrier. Commonly used liquid carriers include xylene, heavy aromatic naphthas, isophorone, and other nonvolatile or slightly volatile organic solvents. For application these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.01 to 95 percent by weight of active ingredient. Also included in the composition are from 1 to 30 percent by weight surface active agent and from 4 to 97.99 percent of one or more of the inert liquid carriers described above. The following are typical EC compositions:

|  | % W/W |
|---|---|
| 1% Emulsifiable Concentrate | |
| Active Ingredient | 1.0 |
| Anionic calcium dodecylbenzene-sulfonate | 4.2 |
| Nonionic polyethoxylated nonylphenol (Mol. Wt. 450–500) | 0.4 |
| Nonionic polyethoxylated nonylphenol (Mol. Wt. 1400–1600) | 1.1 |
| Nonionic paste of 100% poly-with alkylene glycol ether | 0.4 |
| Xylene | 92.9 |
| Total | 100.0 |
| 5% Emulsifiable Concentrate | |
| Active Ingredient | 5.0 |
| Anionic calcium dodecylbenzene-sulfonate | 4.2 |
| Nonionic polyethoxylated nonylphenol (Mol. Wt. 450–500) | 0.4 |
| Nonionic polyethoxylated nonylphenol (Mol. Wt. 1450–1600) | 1.1 |
| Nonionic paste of 100% poly-alkylene glycol ether | 0.4 |
| Xylene | 88.9 |
| Total | 100.0 |
| 10% Emulsifiable Concentrate | |
| Active Ingredient | 10.0 |
| Blend of alkylnaphthalenesulfonate and polyoxyethylene ethers | 4.0 |
| Xylene | 86.0 |
| Total | 100.0 |
| 50% Emulsifiable Concentrate | |
| Active Ingredient | 50.0 |
| Blend of alkylnaphthalenesulfonate and polyoxyethylene ethers | 6.0 |
| Epoxidized soybean oil | 1.0 |
| Xylene | 43.0 |
| Total | 100.0 |
| 75% Emulsifiable Concentrate | |
| Active Ingredient | 75.0 |
| Blend of alkylnaphthalenesulfonate and polyoxyethylene ethers | 4.0 |
| Xylene | 21.0 |
| Total | 100.0 |

Other useful formulations include simple solutions of the active ingredient in a relatively non-volatile solvent such as corn oil, kerosene, propylene glycol, or other organic solvents. This type of formulation is particularly useful for ultra low volume application.

The concentration of the active ingredient in use dilution is normally in the range of about 2% to about 0.1%. Many variations of spraying, dusting, and controlled or slow release compositions in the art may be used by substituting or adding a compound of this invention into compositions known or apparent to the art.

These compositions may be formulated and applied with other suitable active ingredients, including nematicides, insecticides, acaricides, fungicides, plant regulators, herbicides, fertilizers, etc.

In applying the foregoing chemicals, an effective insect controlling amount of active ingredient must be applied, sometimes referred to herein as an insecticidal amount. While the application rate will vary widely depending on the choice of compound, the formulation and mode of application, the plant species being protected and the planting density, a suitable use rate may be in the range of 0.10 to 0.50 kg per hectate, preferably 0.25 to about 1.5 kg/hectare.

The compounds of this invention may be applied by incorporating or applying a formulation thereof to a food source for the insects to be controlled, i.e. the locus where control is required, including application to the above ground portions of plants on which the insects feed, to the soil in which plants are or are about to be planted in order to provide control of soil-borne insects, or in a bait-type formulation for application to surfaces on which insects normally do not feed. When applying the compounds to the soil, the compounds may be broadcast broadly over the planted area or the area to be planted or by limiting the application to a small area or band in the root zone where plants are or are to be planted. When either method of soil application is used, sufficient compound must be applied to provide an insect controlling concentration of the compound in the soil in the root zone. For the present a suitable concentration is about 0.2 to about 50 parts by weight of compound per million parts of soil.

TABLE 1A
COMPOUNDS OF FORMULA I

| Compound No. | R[a] | R[1] | X | Isomer Ratio[b] |
|---|---|---|---|---|
| 1 | A | F | F | 90/10 |
| 2 | A | F | F | 0/100 |
| 3 | B | F | F | 95/5 |
| 4 | C | F | F | 90/10 |
| 5 | D | F | F | 93/7 |
| 6 | E | F | F | 100/0 |
| 7 | F | F | F | 85/15 |
| 8 | G | F | F | 90/10 |
| 9 | G | F | F | 50/50 |
| 10 | H | F | F | 100/0 |
| 11 | I | F | F | 62/38 |
| 12 | J | F | F | 100/0 |
| 13 | K | F | F | 100/0 |
| 14 | A | F | Cl | 100/0 |
| 15 | A | F | H | 100/0 |
| 16 | A | F | OCH$_3$ | 100/0 |
| 17 | C | F | OCH$_3$ | 100/0 |
| 18 | F | F | OCH$_3$ | 100/0 |
| 19 | G | F | OCH$_3$ | 100/0 |
| 20 | A | F | N(CH$_3$)$_2$ | 100/0 |
| 21 | A | Cl | F | 100/0 |
| 22 | C | Cl | F | 100/0 |
| 23 | A | F | phenoxy | 100/0 |
| 24 | C | F | phenoxy | 100/0 |
| 25 | C | F | F | 30/70 |
| 26 | A | H | H | 0/100 |
| 27 | C | H | H | 0/100 |
| 28 | A | H | H | 100/0 |
| 29 | C | H | H | 100/0 |

Footnotes:
[a]A = cis-3-(2-chloro-3,3,3-trifluoropropenyl)-2,2-dimethyl cyclopropyl
B = trans-3-(2-chloro-3,3,3-trifluoropropenyl)-2,2-dimethylcyclopropyl
C = cis-3-(2,2-dichloroethenyl)-2,2-dimethylcyclopropyl
D = trans-3-(2,2-dichloroethenyl)-2,2-dimethylcyclopropyl
E = cis-3-(2,2-dibromoethenyl)-2,2-dimethylcyclopropyl
F = cis-3-(2,2-difluoroethenyl)-2,2-dimethylcyclopropyl
G = trans-3-(2,2-difluoroethenyl)-2,2-dimethylcyclopropyl
H = cis-3-(1,2-dibromo-2,2-dichloroethyl)-2,2-dimethylcyclopropyl
I = trans-3-(1,2-dibromo-2,2-dichloroethyl)-2,2-dimethylcyclopropyl
J = 2,2,3,3-tetramethylcyclopropyl
K = 1-(4-chlorophenyl)-2-methylpropyl

[b]Isomer ratio = $\frac{\text{substituted-pyridin-4-ylmethyl ester}}{\text{substituted-pyridin-2-ylmethyl ester}}$

TABLE IB

| Cmpd. No. | Proton NMR[a,b] | $^{19}$F NMR[b,c] |
|---|---|---|
| 1 | 1.31(s,6H), 1.90-2.25(m,2H), 5.32(t,2H), J$_{HF}$=1.5), 6.89 (dt,1H, J$_{HH}$=8, J$_{HF}$=1.5) | −69.3(s,3F), −90.7(m,2F), −144.5(m,2F) |
| 2 | 1.30(s,3H), 1.33(s,3H), 2.00-2.40(m,2H), 5.20(d,2H, J$_{HF}$=2), 6.90 (dt,1H,J$_{HH}$=8, J$_{HF}$=1.5) | −69.3(s,3F), −89.3(m,1F), −138.9(m,1F), −146.2(m,1F), −157.2(m,1F) |
| 3 | 1.27(s,3H), 1.35(s,3H), 1.82(d,1H,J$_{HH}$=5), 2.43(m,1H), 5.32(t,2H,J$_{HF}$=1.5), 6.17(dt,1H,J$_{HH}$=8, J$_{HF}$=1.5) | |
| 4 | 1.30(s,6H), 1.75-2.20(m,2H), 5.30(t,2H,J$_{HF}$=1.5), 6.20(d,1H,J$_{HH}$=8). | −90.41(m,2F), −143.70(m,2F). |
| 5 | 1.23(s,3H), 1.30(s,3H), 1.65(d,1H,J=6), 2.00-2.40(m,1H), 5.30(t,2H,J$_{HF}$=1.5), 5.63(d,1H,J=8) | |
| 6 | 1.20(s,6H), 1.60-2.10(m,2H), 5.20(t,2H, J$_{HF}$=1.5),6.63 (d,1H,J$_{HH}$=8) | −90.81(m,2F), −143.5(m,1F), −145.8(m,1F). |
| 7 | 1.23(s,6H), 1.70-2.20(m,2H), 4.62(ddd,1H, J$_{HH}$=6,J$_{HF}$=8 and 26), 5.17-5.30(m,2H, J$_{HF}$=1.5). | −86.2(d,1F, J$_{FF}$=43), −90.9(m,2F), −91.6(dd,1F, J$_{FF}$=43, J$_{HF}$=26), −144.2(m,2F). |
| 8 | 1.18(s,3H), 1.27(s,3H), 1.52(dd,1H,J$_{HH}$=6), 2.03(m,1H), 4.10(ddd, 1H,J$_{HH}$=6, J$_{HF}$=8 and 24), 5.32(t,2H,J$_{HF}$=1.5). | |
| 9 | 1.18(s,3H,1.28(s,3H), 1.68(m,1H), 2.03(m,1H), 4.10(ddd,1H,J$_{HH}$=6 J$_{HF}$=8 and 24), 5.22-5.30(d and t, 2H, J$_{HF}$=2). | |
| 10 | 1.30(m,6H), 1.60(m,1H), 1.90-2.30(m,1H), 4.40(t,1H,J=10), 5.30(m,2H). | |
| 11 | 1.30(m,6H), 1.90-2.10(m,2H), 5.00-5.20(m,1H), 5.30(m,2H). | |
| 12 | 1.22(s,6H), 1.27(s,6H), 1.20-1.30(s,1H), 5.27(t,2H,J$_{HF}$=1.5). | |
| 13 | 0.75(d,3H,J=6), 1.06(d,3H,J=6), 2.00-2.30(m,1H), 3.20(m,1H), 5.28(t,2H,J$_{HF}$=1.5), 7.28(s,4H). | |
| 14 | 1.30(bs,6H), 1.80-2.30(m,2H), 5.20(t,2H, J$_{HF}$=1.5),6.92 (bd,1H,J=8) | −69.3(s,3F), −89.1(dd,1F, J$_{FF}$=26 and 30), −132.1(d,1F, J$_{FF}$=30), −139.2(d,1F, J$_{FF}$=26). |
| 15 | 1.33(s,6H), 1.80-2.40(m,2H), 5.30(t,2H, J$_{HF}$=1.5),6.80 (bd,1H,J=8), 7.97(m,1H). | −69.2(s,3F), −87.7(dd,1F, J$_{FF}$=22 and 30), −122.37(dd,1F, J$_{FF}$=30,J$_{HF}$=2.5) −140.42(dd,1F, J$_{FF}$=22,J$_{HF}$=2.5). |
| 16 | 1.32(s,6H), 1.90-2.40(m,2H), 4.00(s,3H), 5.27(bs,2H), | −69.28(s,3F), −94.15(dd,1F, J$_{FF}$=22 and 31), −144.38(dd,1F. |

TABLE IB-continued

| Cmpd. No. | Proton NMR[a,b] | 19F NMR[b,c] |
|---|---|---|
|  | 6.90(bd,1H) | $J_{FF}=31, J_{HF}=2$), −154.1(dd,1F, $J_{FF}=22, J_{HF}=3$). |
| 17 | 1.25(s,6H), 1.60-2.20(m,2H), 4.00(s,3H), 5.28(bs,2H), 6.25(d,1H,J=8). | −94.23(dd,1F, $J_{FF}=22$ and 31), −144.28(dd,1F, $J_{FF}=31, J_{HF}=2$), −153.98(dd,1F, $J_{FF}=22, J_{HF}=3$). |
| 18 | 1.23(s,6H) 1.60-2.10(m,2H), 4.00(s,3H), 4.20-4.90(m,1H), 5.25(t,2H, $J_{HF}=1.5$). |  |
| 19 | 1.15(s,3H), 1.32(s,3H), 1.50-2.20(m,2H), 3.98(s,3H), 4.10(ddd,1H, $J_{HH}=6$, $J_{HF}=8$ and 24), 5.25(m,2H). |  |
| 20 | 1.28(s,6H), 1.90-2.40 (m,2H), 3.05(d,6H,J=2), 5.20t,2H,J=1.5), 6.55(d,1H,J=8). | −69.37(s,3F), −92.61(dd,1F, $J_{FF}=25$ and 33), −137.00(dt,1F, $J_{FF}=33, J_{HF}=2$, −159.12(dd,1F, $J_{FF}=25, J_{HF}=6$). |
| 21 | 1.35(s,6H), 1.7-2.2(m,2H), 5.42 (d,2H), 6.93 (bd,1H). | −69.22 (3F), −70.67 (2F) |
| 22 | 1.32(s,6H), 1.6-2.25(m,2H), 5.38 (d,2H), 6.22 (d,1H). | −70.80 |
| 23 | 1.42(d,6H), 2.0-2.5(m,2H), 5.32 (s,2H), 6.8-7.8 (m,5H). | −69.12(d,3F), −94.5(m,1F), −146.50(m,1F), −155.6(m,1F). |
| 24 | 1.31(s,6H), 2.0-2.35(m,2H), 5.31(s,2H), 6.2-−6.4(m,1H), 7.0-7.6(m,5H). | −94.6(m,1F), −146.50(m,1F), −155.8(m,1F). |
| 25 | 1.28(s,6H), 1.85-2.3(m,2H), 5.35 (dt,2H), 6.38 (m,1H). | −83.22(m,0.7F), −90.43(m,0.6F), −138.7(m,0.7F), −143.59(m,0.6F), −146.11(m,0.7F), −157.10(m,0.7F). |
| 26 | 1.33(bs,6H),2.0-2.4(m,2H), 5.2 (bs,2H), 6.8-8.0(m,4H). | −67.33(d,1F, J=8Hz), −69.16 (s,3F). |
| 27 | 1.28(s,6H), 2.0-2.2(m,2H), 5.15 (bs,2H), 6.3 (d,1H), 6.8-8.0 (m,3H). | −67.40(d,1F, $J_{HF}=8Hz$). |
| 28 | 1.33(d,6H), 1.8-2.2(m,2H), 5.15 (bs,2H), 6.8-7.3 (m,3H), 8.27 (d,1H). | −67.97(d,1F), −69.3(s,3F). |
| 29 | 1.30(bs,6H), 1.75-2.2(m,2H), 5.15(bs,2H), 6.2 (bd,1H), 6.8-8.2(m,3H). | −68.0(d,1F) |

TABLE 1C
COMPOUNDS OF FORMULA II

| Cmpd. of Example | R¹ | X | Q | Proton NMR[a] | 19F NMR[a] |
|---|---|---|---|---|---|
| 6 | F | NHNH₂ | OH |  | −94.95(dd,1F, $J_{FF}=4$ and 32) −148.85(d,1F, $J_{FF}=32$), 160..69(d,1F, $J_{FF}=4$) |
| 7 | F | Cl | OH | 2.50(bs,1H), 4.90(bs,2H). | −88.01(dd,1F, $J_{FF}=24$ and 29) −124.40(dd,1F, $J_{FF}=4$ and 29), −142.51(dd,1F, $J_{FF}=4$ and 24). |
| 9 | F | H | OH | 2.55(bm,1H), 4.90(bs,2H), 7.20-7.90 (m,1H), | −89.50(t,1F, $J_{FF}=28$), −133.95(dd,1F, $J_{FF}=30$ and 2), −141.34(d,1F, $J_{FF}=28$). |
| 11 | F | OCH₃ | OH | 3.07(bs,1H), 4.00(s,3H), 4.83(bs,2H). | −94.80(dd,1F, $J_{FF}=22$ and 30), −146.36(d,1F, $J_{FF}=30$), −155.86(d,1F, $J_{FF}=22$). |
| 13 | F | N(CH₃)₂ | OH | 3.05(dd,7H, J=2 and 4), 4.75(t,2H, J=1). | −93.35(dd,1F, $J_{FF}=25$ and 29) −138.45(d,1F, $J_{FF}=32$), −160.43(dd,1F, $J_{FF}=3$ and 25). |
| 15 | Cl | F | OH[d] | 2.67(t,1H), 4.92(d,2H). | −71.19(s,2F)[e] |
| 18 | F | phenoxy | OH[f] | 4.8-4.9(t, 1H),5.5(bs, 2H), 6.7-7.4(m,5H). | −93.0(m,0.2F), −93.42(m,0.8F), −140.9(m,0.2F), −142.5(m,0.8F), −145.3(m,0.2F), |
| 20 | H | H | Br[g] | 4.47(s,2H), 6.75-8.0(m,3H). | −66.9(d,1F) |
| 22 | H | H | Br[h] | 4.77(s,2H), 7.05-7.30 (m,2H), 8.23 (d,1H). | −68.13(s,1F). |

[a] See footnotes for Table 1B.
[d] 100% 4-hydroxymethyl substituent
[e] Reference compound was hexafluorobenzene and solvent was CDCl₃
[f] Ratio 4-hydroxymethyl compound/2-hydroxymethylcompound was 80/20, however, esters prepared from this mixture were isolated by chromatography and consisted 100% of the pyridin-4-ylmethyl isomer.
[g] 100% 2-bromomethyl-6-fluoropyridine
[h] 100% 4-bromomethyl-2-fluoropyridine

TABLE 2
INITIAL ACTIVITY AS SOIL INSECTICIDES

| | Percent Mortality | | | | |
|---|---|---|---|---|---|
| Cmpd. No. | 4 ppm | 2 ppm | 1 ppm | 0.5 ppm | 0.25 ppm |
| 1 | 100[a] | 100[a] | 90[a] | 93[a] | 40 |
| 2 | 85 | 50 | 35 | 20 | 15 |
| 3 | 100[a] | 100 | 85 | 40 | 15 |
| 4 | 100[b] | 93[b] | 45 | 45 | 5 |
| 5 |  |  |  |  |  |
| 6 |  |  |  |  |  |
| 7 | 100 | 100[a] | 85 | 65 | 15 |
| 8 | 95[a] | 90[a] | 55 | 25 | 30 |
| 9 | 100 | 70 | 65 | 30 | 20 |
| 10 |  | 45 | 30 | 20 | 5 |
| 11 | 90 | 65 | 30 | 35 | 25 |
| 12 | 95 | 30 | 10 | 5 | 5 |
| 13 |  |  |  |  |  |
| 14 | 100 | 90 | 30 | 15 | 10 |
| 15 | 100 | 85 | 45 | 5 | 0 |
| 16 | 95 | 90 | 90 | 50 | 5 |
| 17 | 73 | 17 | 7 | 0 | 0 |
| 18 | 90 | 55 | 10 | 0 | 0 |
| 19 | 80 | 10 | 5 | 0 | 0 |

TABLE 2-continued
INITIAL ACTIVITY AS SOIL INSECTICIDES

| | Percent Mortality | | | | |
|---|---|---|---|---|---|
| Cmpd. No. | 4 ppm | 2 ppm | 1 ppm | 0.5 ppm | 0.25 ppm |
| 20 | 100 | 100 | 45 | 5 | 5 |
| 21 | 100 | 90 | 75 | 70 | 50 |
| 22 | 95 | 80 | 40 | 30 | 10 |
| 23 | 100 | 90 | 65 | 65 | 55 |
| 24 | 95 | 65 | 35 | 25 | 10 |
| 25 | 100 | 85 | 60 | 50 | 35 |
| 26 | 90 | 85 | 85 | 65 | 55 |
| 27 | 100 | 60 | 50 | 45 | 25 |

[a]Average of 2 results
[b]Average of 3 results

TABLE 3
RESIDUAL ACTIVITY AS SOIL INSECTICIDES

| | Percent Mortality | | | |
|---|---|---|---|---|
| | 7 Days | | 14 Days | 28 Days | 42 Days |
| Cmpd. No. | 8 ppm | 4 ppm | 4 ppm | 4 ppm | 2 ppm |
| 1 | 100 | 100[a] | 90[a] | 80[a] | 80 |
| 2 | | 0 | | | |
| 3 | 100 | 90[a] | 80[a] | 25[a] | |
| 4 | | 100[a] | 85[a] | 75[a] | 0 |
| 7 | 100 | 95[a] | 100[a] | 90[a] | 15 |
| 8 | 100 | 50 | 0 | 0 | |
| 9 | 20 | 5[a] | | | |
| 11 | | 20 | | | |
| 12 | | 10 | | | |
| 14 | | 20 | | | |
| 15 | | 5 | | | |
| 16 | | 90 | 90 | 40 | |
| 17 | | 16 | | | |
| 18 | | 37 | 33 | | |
| 19 | | 0 | | | |
| 20 | | 10 | | | |
| 21 | | 95 | 55 | 20 | |
| 22 | | 75 | 70 | 25 | |
| 23 | | 65 | 45 | — | |
| 24 | | 100 | 65 | — | |
| 25 | | 100 | 95 | 90 | |
| 26 | | 90 | 95 | 45 | |
| 27 | | 65 | 50 | 40 | |

Footnotes: See Table 2

TABLE 4
RESULTS OF FOLIAR INSECTICIDE SCREEN AT 1000 ppm

| | Percent Mortality | | | |
|---|---|---|---|---|
| Cmpd. No. | Mexican Bean Beetle[a] | Pea Aphid[b] | Southern Armyworm[c] | Twospotted Spider Mite[d] |
| 1 | 100 | 100 | 100 | 0 |
| 2 | 0 | 0 | 0 | 0 |
| 3 | 100 | 100 | 100 | 0 |
| 4 | 100 | 100 | 100 | 0 |
| 5 | 100 | 100 | 100 | 0 |
| 6 | 100 | 100 | 100 | 0 |
| 7 | 0 | 0 | 20 | 0 |
| 8 | 0 | 0 | 0 | 0 |
| 9 | 0 | 50 | 40 | 0 |
| 10 | 100 | 40 | 45 | 0 |
| 11 | 100 | 100 | 100 | 0 |
| 12 | 0 | 0 | 0 | 0 |
| 13 | 95 | 100 | 0 | 0 |
| 14 | 50 | 100 | 100 | 0 |
| 15 | 100 | 0 | 0 | 0 |
| 16 | 100 | 100 | 100 | 0 |
| 17 | 100 | 100 | 100 | 0 |
| 18 | 100 | 100 | 100 | 0 |
| 19 | 65 | 95 | 50 | 80 |
| 20 | 0 | 100 | 100 | 100 |
| 21 | 100 | 100 | 50 | 0 |
| 22 | 100 | 100 | 50 | 0 |
| 23 | 0 | 0 | 0 | 0 |
| 24 | 0 | 0 | 0 | 0 |
| 25 | 100 | 100 | 60 | 100 |
| 26 | 0 | 0 | 0 | 0 |
| 27 | 0 | 0 | 0 | 0 | a. *Epilachna varivestis*
b. *Acyrthosiphon pisum*
c. *Spodoptera eridania*
d. *Tetranychus urticae*

We claim:

1. A compound of the formula

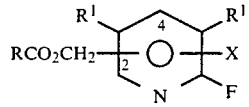

in which X is hydrogen, halogen or $C_{1-2}$alkoxy; R is 3-(2-chloro-3,3,3-trifluoropropenyl)-2,2-dimethylcyclopropyl; 3-(2,2-dibromo- or difluoro-ethenyl)-2,2-dimethylcyclopropyl; 3-(1,2-dibromo-2,2-dichloroethyl)-2,2-dimethylcyclopropyl; or 2,2,3,3-tetramethylcyclopropyl; $R^1$ is hydrogen or a halogen; X is at position 2 or 4 of the pyridinyl ring; and the carboxylate group is at the other of position 2 or 4.

2. A compound of claim 1 in which X is at position 2 of the pyridinyl ring and the carboxylate moiety is attached at position 4.

3. A compound of the formula

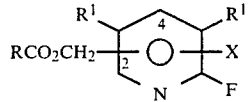

in which X is $C_{1-2}$alkoxy; R is 3-(2-chloro-3,3,3-trifluoropropenyl)-2,2-dimethylcyclopropyl; 3-(2,2-dihaloethenyl)-2,2-dimethylcyclopropyl; 3-(1,2-dibromo-2,2-dichloroethyl)-2,2-dimethylcyclopropyl; or 2,2,3,3-tetramethylcyclopropyl; $R^1$ is hydrogen or a halogen; X is at position 2 or 4 of the pyridinyl ring; and the carboxylate group is at the other of position 2 or 4.

4. A compound of claim 14 in which X is at position 2 of the pyridinyl ring and the carboxylate moiety is attached at position 4.

5. A compound of claim 1 in which R is cis-3-(2-chloro-3,3,3-trifluoropropenyl)-2,2-dimethylcyclopropyl.

6. A compound of claim 1 in which R is cis-3-(2,2-dichloroethenyl)-2,2-dimethylcyclopropyl.

7. A compound of claim 1 in which $R^1$ is a halogen.

8. A compound of claim 1 in which X is a halogen.

9. A compound of claim 1 in which X is methoxy.

10. A compound of claim 1 in which X and $R^1$ are the same or different halogens.

11. The compound, 2,3,5,6-tetrafluoropyridin-4-yl)methyl cis-3-(2-chloro-3,3,3-trifluoropropenyl)-2,2-dimethylcyclopropanecarboxylate.

12. The compound, 2,3,5,6-tetrafluoropyridin-4-yl)methyl trans-3-(2-chloro-3,3,3-trifluoropropenyl)-2,2-dimethylcyclopropanecarboxylate.

13. The compound, 3,5,6-trifluoro-2-methoxypyridin-4-yl)methyl cis-3-3-(2-chloro-3,3,3-trifluoropropenyl)-2,2,-dimethylcyclopropanecarboxylate.

14. The compound, 2,6-dichloro-3,5-difluoropyridin-4-yl)methyl cis-3-(2-chloro-3,3,3-trifluoropropenyl)-2,2-dimethylcyclopropanecarboxylate.

15. The compound, 2,3,5,6-tetrafluoropyridin-4-yl)methyl cis-3-(2,2-dichloroethenyl)-2,2-dimethylcyclopropanecarboxylate.

16. The compound, 2,6-dichloro-3,5-difluoropyridin-4-yl)methyl cis-3-(2,2-dichloroethenyl)-2,2-dimethylcyclopropanecarboxylate.

17. The compound, 2,3,5,6-tetrafluoropyridin-4-yl)methyl cis-3-(2,2-difluoroethenyl)-2,2-dimethylcyclopropanecarboxylate.

18. The compound, 3,5,6-trifluoro-2-methoxypyridin-4-yl)methyl trans-3-(2,2-difluoroethenyl)-2,2-dimethylcyclopropanecarboxylate.

19. An insecticidal composition comprising an insecticidal effective amount of a compound of the formula

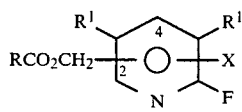

in which X is hydrogen, halogen or $C_{1-2}$alkoxy; R is 3-(2-chloro-3,3,3-trifluoropropenyl)-2,2-dimethylcyclopropyl; 3-(2,2-dihaloethenyl)-2,2-dimethylcyclopropyl; 3-(1,2-dibromo-2,2-dichloroethyl)-2,2-dimethylcyclopropyl; or 2,2,3,3-tetramethylcyclopropyl; $R^1$ is hydrogen or a halogen; X is at position 2 or 4 of the pyridinyl ring; and the carboxylate group is at the other of position 2 or 4 in admixture with at least one agriculturally acceptable carrier, vehicle, or adjuvant.

20. An insecticidal composition of claim 3 in which X is at position 2 of the pyridinyl ring and the carboxylate moiety is attached at position 4.

21. A method for controlling insects by applying to the locus where control is desired, an insecticidal effective amount of a compound of the formula

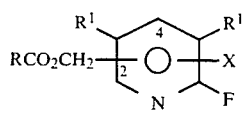

in which X is hydrogen, halogen or $C_{1-2}$alkoxy; R is 3-(2-chloro-3,3,3-trifluoropropenyl)-2,2-dimethylcyclopropyl; 3-(2,2-dihaloethenyl)-2,2-dimethylcyclopropyl; 3-(1,2-dibromo-2,2-dichloroethyl)-2,2-dimethylcyclopropyl; or 2,2,3,3-tetramethylcyclopropyl; $R^1$ is hydrogen or a halogen; X is at position 2 or 4 of the pyridinyl ring; and the carboxylate group is at the other position 2 or 4.

22. The method of claim 5 by applying to the locus where control is desired, an insecticidal effective amount of the compound in which X is at position 2 of the pyridinyl ring and the carboxylate moiety is attached at position 4.

23. A method for controlling acarids by applying to the locus where control is desired, an acaricidal effective amount of a compound of the formula

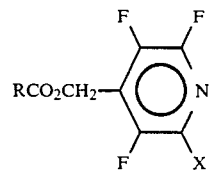

in which X is methoxy and R is trans-3-(2,2-difluoroethenyl)-2,2-dimethylcyclopropyl.

24. A method for controlling acarids by applying to the locus where control is desired, an acaricidal effective amount of a compound of the formula

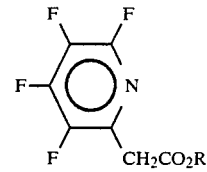

where R is cis-3-(2,2-dichloroethenyl)-2,2-dimethylcyclopropyl.

* * * * *

UNITED STATES PATENT AND TRADEMARK OFFICE
CERTIFICATE OF CORRECTION

PATENT NO. : 4,701,464

DATED : October 20, 1987

INVENTOR(S) : Richard B. Phillips, Ernest L. Plummer & John F. Engel

It is certified that error appears in the above-identified patent and that said Letters Patent is hereby corrected as shown below:

Column 3, line 43, "3,3-trifluoropenyl)" should read --3,3,3-trifluoropropenyl)--. Column 8, Example 16, line 62, "By The" should read --By the--. Column 10, Example 21, line 38, "boxylic, acid" should read --boxylic acid--. Column 11, line 19, "The ir, proton nmr, and 19c" should read --The ir, proton nmr, and 19F--. Column 11, line 54, "not been effected" should read --not been affected--. Column 12, line 17, "1400 cup," should read --1400ml cup--. Column 18, line 12, "with alkylene glycol", should read --alkylene glycol--. In the claims, claim 4, line 50, "claim 14" should read --claim 3--. Claim 13, line 2, "cis-3-3" should read --cis-3--. Claim 22, line 16, "claim 5" should read --claim 21.

Signed and Sealed this

Twentieth Day of September, 1988

Attest:

DONALD J. QUIGG

Attesting Officer          Commissioner of Patents and Trademarks

UNITED STATES PATENT AND TRADEMARK OFFICE
CERTIFICATE OF CORRECTION

PATENT NO. : 4,701,464

DATED : October 20, 1987

INVENTOR(S) : Richard B. Phillips, Ernest L. Plummer, and John F. Engel

It is certified that error appears in the above—identified patent and that said Letters Patent is hereby corrected as shown below:

In claim 20, "of claim 3" should read --of claim 19-- .

Signed and Sealed this

Tenth Day of October, 1989

Attest:

DONALD J. QUIGG

Attesting Officer

Commissioner of Patents and Trademarks